US007656525B2

(12) United States Patent
Zhao et al.

(10) Patent No.: US 7,656,525 B2
(45) Date of Patent: Feb. 2, 2010

(54) FIBER OPTIC SERS SENSOR SYSTEMS AND SERS PROBES

(75) Inventors: Yiping Zhao, Statham, GA (US); Yongjun Liu, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 342 days.

(21) Appl. No.: 11/834,233

(22) Filed: Aug. 6, 2007

(65) Prior Publication Data

US 2008/0144026 A1 Jun. 19, 2008

Related U.S. Application Data

(63) Continuation-in-part of application No. 11/495,980, filed on Jul. 28, 2006, now Pat. No. 7,583,379, application No. 11/834,233, which is a continuation-in-part of application No. 11/376,661, filed on Mar. 15, 2006, application No. 11/834,233, which is a continuation-in-part of application No. 11/256,385, filed on Oct. 21, 2005.

(60) Provisional application No. 60/835,673, filed on Aug. 4, 2006, provisional application No. 60/703,110, filed on Jul. 28, 2005, provisional application No. 60/620,810, filed on Oct. 21, 2004, provisional application No. 60/662,089, filed on Mar. 15, 2005.

(51) Int. Cl.
   *G01J 3/44* (2006.01)

(52) U.S. Cl. ............... 356/301; 436/164; 436/171; 435/288.7; 435/287.1

(58) Field of Classification Search ................ 356/301; 435/288.7, 287.1, 287.2; 436/164, 171; 422/681
See application file for complete search history.

(56) References Cited

U.S. PATENT DOCUMENTS

| 5,693,152 | A | * | 12/1997 | Carron | 148/271 |
|---|---|---|---|---|---|
| 6,180,415 | B1 | | 1/2001 | Schultz et al. | 436/518 |
| 6,376,177 | B1 | | 4/2002 | Poponin | 435/6 |
| 6,707,548 | B2 | * | 3/2004 | Kreimer et al. | 356/301 |
| 6,888,629 | B1 | * | 5/2005 | Boss et al. | 356/301 |
| 7,139,072 | B1 | * | 11/2006 | Boss et al. | 356/301 |
| 7,151,598 | B2 | * | 12/2006 | Poponin | 356/301 |
| 7,192,703 | B2 | | 3/2007 | Sun et al. | |
| 7,267,948 | B2 | * | 9/2007 | Vo-Dinh | 435/6 |

(Continued)

FOREIGN PATENT DOCUMENTS

EP 0 261 642 9/1987

(Continued)

OTHER PUBLICATIONS

Aizpurua, et al; "Optical Properties of Coupled Metallic Nanorods for Field-enhanced Spectroscopy"; The American Physical Society; 2005; 13 pages.

(Continued)

*Primary Examiner*—L. G Lauchman
(74) *Attorney, Agent, or Firm*—Thomas, Kayden, Horstemeyer & Risley, LLP (57) ABSTRACT

Fiber optic surface-enhanced Raman spectroscopic (SERS) systems (also referred to as "SERS system"), portable SERS systems, SERS probes, and methods of using the SERS systems and SERS probes to detect an analyte, are disclosed.

11 Claims, 6 Drawing Sheets

U.S. PATENT DOCUMENTS

| | | | |
|---|---|---|---|
| 7,361,313 | B2 | 4/2008 | Chan et al. |
| 7,393,692 | B2* | 7/2008 | Farquharson et al. ....... 436/171 |
| 7,397,558 | B2 | 7/2008 | Kamins et al. |
| 7,400,395 | B2 | 9/2008 | Chan et al. |
| 7,420,672 | B2* | 9/2008 | Wang et al. ............. 356/301 |
| 7,428,046 | B2* | 9/2008 | Wang et al. ............. 356/301 |
| 7,583,379 | B2* | 9/2009 | Zhao et al. ............. 356/301 |
| 2004/0174520 | A1* | 9/2004 | Premasiri et al. ........ 356/301 |
| 2005/0266584 | A1* | 12/2005 | Farquharson ........... 436/171 |
| 2006/0017917 | A1* | 1/2006 | Cullum et al. ........... 356/301 |
| 2006/0147927 | A1 | 7/2006 | Geddes et al. |
| 2007/0153269 | A1* | 7/2007 | Wang et al. ............. 356/301 |
| 2008/0024777 | A1* | 1/2008 | Wang et al. ............. 356/301 |
| 2008/0059135 | A1 | 3/2008 | Murugkar et al. |
| 2008/0192247 | A1* | 8/2008 | Zerbi et al. ............. 356/301 |
| 2008/0198376 | A1* | 8/2008 | Poponin ................ 356/301 |
| 2009/0086202 | A1* | 4/2009 | Wang et al. ............. 356/301 |

FOREIGN PATENT DOCUMENTS

| | | |
|---|---|---|
| EP | 1 953 536 | 6/2008 |
| WO | 2004059279 | 7/2004 |
| WO | WO 2006/005111 | 1/2006 |
| WO | WO 2006/066180 | 6/2006 |
| WO | 2006/137885 | 12/2006 |
| WO | 2007059514 | 5/2007 |
| WO | WO 2007/135593 A1 | 11/2007 |
| WO | 2008045114 | 4/2008 |

OTHER PUBLICATIONS

Chaney, et al; "Aligned Silver Nanorod Arrays Produce High Sensitivity Surface-enhanced Raman Spectroscopy Substrates"; American Institute of Physics; 2005; 3 pages.

Coldiron, et al; "Nanotechnology in Cancer"; http://www.concana.com/Nanotechnology.htm; Copyright 2007-2008; 5 pages.

Faulds, et al; "Evaluation of Surface-enhanced Resonance Raman Scattering for Quantitative DNA Analysis"; http:// www.nano-biology.net/showabstract.php?pmid=14719891; 2004; 1 page.

Gu, et al; "Optimum Length of Silver Nanorods for Fabrication of Hot Spots"; American Chemical Society; 2007; 4 pages.

Hafner; "Plasmonics: Gold Nanoparticles are Shaped for Effect"; http://www.laserfocusworld.com/articles/ article_display.html?id=252462; 2006; 4 pages.

Kim; "Surface Plasmon Resonances of Noble Metal Nanorods and Nanoparticles"; Sungkyunkwan University; May 29, 2007; 29 pages.

Murphy, et al; "Chemical Sensing and Imaging with Metallic Nanorods"; The Royal Society of Chemistry; 2008; 14 pages.

Nikoobakht, et al; "Surface-Enhanced raman Scattering Studies on Aggregated Gold Nanorods"; American Chemical Society; 2003; 7 pages.

Shuyi, et al; "An Approach to Self-Cleaning SERS Sensors by Arraying Au Nanorods on TiO2 Layer"; http://adsabs.harvard.edu/abs/2007SPIE.6647E..13L; 2007; 2 pages.

Suzuki, et al; "Physically Self-Assembled Ag nanorod Arrays for Tunable Plasmonic Sensors"; The Surface Science Society of Japan; 2005; 4 pages.

Suzuki, et al; "Vapor Phase Growth of al Whiskers Induced by Glancing Angle Deposition at High Temperature"; American Institute of Physics; 2006; 3 pages.

Uechi, et al; "Phtochemical and Analytical Applications of Gold Nanoparticles and Nanorods Utilizing Surface Plasmon Resonance"; Anal Bioanal Chem; 2008; 11 pages.

Yao, et al; "A Complementary Study of Surface-enhanced Raman Scattering and Metal Nanorod Arrays"; Pure Appl. Chem, vol. 72; 2000; 8 pages.

Yao, et al; "Electronic Properties of Metal Nanorods Probed by Surface-enhanced Raman Spectroscopy"; Chem. Commun.; The Royal Society of Chemistry; 2000; 2 pages.

Wang, et al.; Layer uniformity of glancing angle deposition; Vaccum; vol. 78, Issue 1, Apr. 4, 2005, pp. 107-111.

Schubert, et al.; Nanostructure fabrication by glancing angle ion beam assisted deposition of silicon; Applied Physics A: Materials Science & Processing; vol. 81, No. 3 / Aug., 2005.

Brett, et al.; Glancing Angle Deposition, An Overview of Thin Films and GLAD; http://www.ece.ualberta.ca/~glad/glad.html; 2006.

Gish, et al.; Evaluation of silver nanostructures fabricated using glancing angle deposition as localized surface plasmon resonance biosensors; Nanotech 2007 Conference Program Abstract.

Zhao, et al.; Designing Nanostructures by Glancing Angle Deposition; Proceedings of SPIE; vol. 5219; Nanotubes and Nanowires; Invited Paper, pp. 59-73.

Katherine A. Willets and -Richard P. Van Duyne; Localized Surface Plasmon Resonance Spectroscopy and Sensing; Annual Review of Physical Chemistry; vol. 58: 267-297 (volume publication date May 2007); First published online as a Review in Advance on Oct. 26, 2006.

ARS Project: 408043—Annual Reports for 2004-2007; USDA Agricultural Research Service.

Big Discovery Symposium 2006; UC Santa Barbara; Epigenetic Enzymes and Therapies; slide show.

Kathy Kincade; Raman Spectroscopy: SERS and Silver Nanorods Quickly Reveal Viral Structures; Laser Focus World; Jan. 1, 2007.

Kathy Kincade; Optoelectronic Applications: Nanophotonics—An "Old" Technique Finds New Life in the Nano World; Laser Focus World; Oct. 1, 2006.

Kawai, et al.; Raman Spectroscopic Probes Withstand Hostile Environments; Laser Focus World; Jun. 1, 2005.

Amri, et al.; Adenine and RNA in Mineral Samples. Surface-Enhanced Raman Spectroscopy (SERS) for Picomole Detections; Spectrochimica Acta Part A 59 (2003) pp. 2645-2654.

Stuart, et al.; In Vivo Glucose Measurement by Surface-Enhanced Raman Spectroscopy; Anal. Chem. 2006, 78, pp. 7211-7215.

Faulds, et al.; DNA Detection by Surface Enhanced Resonance Raman Scattering (SERRS); The Royal Society of Chemistry 2005; Analyst, 2005, 130, pp. 1125-1131.

Bell, et al.; Surface-Enhanced Raman Spectroscopy (SERS) for Sub-Micromolar Detection of DNA/RNA Mononucleotides; J. Am. Chem. Soc. 2006, 128, pp. 15580-15581.

Yun Wei Charles Cao, et al.; Nanoparticles with Raman Spectroscopic Fingerprints for DNA and RNA Detection; Science, 297; 2002; pp. 1536-1540.

Mecham, et al.; Research on Bettering Surveillance of Arboviral Threats, Using West Nile Virus as a Model; USDA Agricultural Research Service; abstract.

Gish, et al.; Evaluation of Silver nanostructures Fabricated Using Glancing Angle Deposition as Localized Surface Plasmon Resonance Biosensors; The Nanotechnology Conference and Trade Show; Boston, Jun. 1-5, 2008; abstract.

Wang, et al.; Layer Uniformity of Glancing Angle Deposition; Vacuum; 78; 2005; pp. 107-111.

Schubert; Nanostructure Fabrication by Blancing Angle Ion Beam Assisted Deposition of Silicon; Appl. Physc. A81, 481-486 (2005).

Willets, et al.; Localized Surface Plasmon Resonance Spectroscopy and Sensing; Annu. Rev. Phys. Chem 2007; 52; 267-297.

Prokes, et al.; Enhanced Plasmon Coupling in Crossed Dielectric/Metal Nanowire Composite Geometries and Applications to Surface-Enhanced Raman Spectroscopy; Appl. Physc. Lett; 90; 2007; 3 pages.

D. Keith Roper; Determining Surface Plasmon Resonance Response Factors for Deposition onto Three-Dimensional Surfaces; Chemical Engineering Science; 62; 2007; pp. 1988-1996.

Takemoto, et al.; A Surface Plasmon Resonance Assay for the Binding of Influenza Virus Hemagglutinin to Its Sialic Acid Receptor; Virology; 217; 452-458 (1996) Article No. 0139.

Hardy, et al.; Valency of Antibody Binding to Enveloped Virus Particles as Determined by Surface Plasmon Resonance; Journal of Virology; Jan. 2003; p. 1649-1652; vol. 77, No. 2.

Publication US2004/0224321; Published Nov. 11, 2004; Nicolau, et al.; Micro/Nano-Structures Fabricated by Laser Ablation for Micro-Array Applications.

A Graded Improvement; Science, vol. 319; Feb. 29, 2008, p. 1163.

Kim; et al.; Light-Extraction Enhancement of GaInN Light-Emitting Diodes by Graded-Refractive-Index Indium Tin Oxide Anti-Reflection Contact; Adv. Mater. 2008, 20, pp. 801-804.

Robbie, et al.; Sculptured Thin Films and Glancing Angle Deposition: Growth Mechanics and Applications; J. Va. Sci. Technol. A 15(3), May/Jun. 1997; pp. 1460-1465.

Robbie, et al.; Fabrication of Thin Films With Highly Porous Microstructures; J. Va. Sci. Technol. A 13(3), May/Jun. 1995; pp. 1032-1035.

Robbie, et al.; First Thin Film Realization of a Helicoidal Bianisotropic Medium; J. Vac. Sc. Technol. A 13(6), Nov./Dec. 1995; pp. 2991-2993.

Huang, et al.; Single-Domain Antibody-Conjugated nanoaggregate-Embedded Beads for Targeted Detection of Pathogenic Bacteria; Chem. Eur. J. 2009, 00, 0-0; pp. 1-6.

Bentley; "Microsensors: Invisible Watchdogs to Keep Us Safe and Well"; http://www.solve.csiro.au/0805/article1.htm; Aug. 2005; 4 pages.

Campion, et al.; "Surface-enhanced Raman scattering"; Chemical Society Reviews, vol. 27; 1998; 10 pages.

Carillo; "Sers nanoparticles: a new optical detection modality for rapid tests"; http://www.cli-online.com/en/featured-articles/sers-nanoparticles-a-new-optical-detection-modality-for-rapid-tests/trackback/1/index.html; Copyright 2004-2007; 4 pages.

Clin; "Applications of Nanobiotechnology in Clinical Diagnostics"; http://www.clinchem.org/cgi/content/full/53/11/2002; 2007; 1 page.

Driskell, et al.; "Low-Level Detection of Viral Pathogens by a Surface-Enhanced Raman Scattering Based Immunoassay"; 2005; 8 pages.

Fischer, et al.; "Heightened sense for sensing: recent advances in pathogen immunoassay sensing platforms"; Lawrence Livermore National Laboratory; Feb. 06, 2007; 13 pages.

Goeller, et al.; "Discrimination of Bacteria and Bacteriophages by Raman Spectroscopy and Surface-Enhanced Raman Spectroscopy"; Society for Applied Spectroscopy; vol. 61; Nov. 07, 2007; 7 page.

Gordon, et al.; "Plasmonic Sensors Based on Nano-Holes: Technology and Integration"; Micro and Nanotechnologies for Space, Defense, and Security II; vol. 6959; 2008; 6 pages.

Grabar, et al.; "Preparation and Characterization of Au Colloid Monolayers"; The Pennsylvania State University; vol. 67 Feb. 15, 1995; 9 pages.

Grow, et al.; "Evaluation of the Doodlebug: A Biochip for Detecting Waterborne Pathogens"; http://www.iwapublishing.com/template.cfm?name=isbn1843396688; Jun. 01, 2003; 1 page.

Grow, et al.; "New biochip technology for label-free detection of pahogens and their toxins"; Biopraxis, Inc.; Journal of Microbiological Methods; 2003; 13 pages.

Gu, et al.; "Biofunctional magnetic nanoparticles for protein separation and pathogen detection"; ChemComm; Jan. 19, 2006; 9 pages.

Hou, et al.; "Rapid Chip-Scale Detection by Micro-Spiral Flow and Surface Enhanced Raman Scattering"; http://aiche.confex.com/aiche/2006/techprogram/P66060.HTM; Nov. 15, 2006; 2 pages.

Kao, et al.; "Surface-Enhanced Raman Detection on Metalized Nanostructured Poly(p-xylylene) Films"; Advanced Materials; 2008; 4 pages.

Koo, et al.; "Single-molecule detection of biomolecules by surface-enhanced coherent anti-Stokes Raman scattering"; Optics Letters; vol. 30; May 01, 2005; 3 pages.

Richards; "Nano-optics: Imaging beyond the Diffraction Limit, Fluorescence and Lifetime Modification, Surface Enhanced Raman Scattering"; http://www.opticalproteomics.org/research/nanooptics.php#sers; 2 pages.

Service; "Fast, Sensitive Scan Targets Anthrax"; http://www.sciencemag.org/cgi/content/full/308/5718/45?ck=nck; vol. 308; Apr. 01, 2005; 5 pages.

Stokes, et al.; "Detection of *E. coli* using a microfluidics-based antibody biochip detection system"; Advanced Monitoring Development Group; Nov. 13, 2000; 7 pages.

Taurozzi; "Sers-Active Silver Nanoparticle Arrays on Track Etch Membrane Support as Flow-through Water Quality Sensors"; http://aiche.confex.com/aiche/2006/techprogram/P59895.HTM; Nov. 15, 2006; 3 pages.

Tay; "Applications of Enhanced Raman Spectroscopy i Biological Sciences"; Institute for Microstructural Sciences; 2005; 12 pages.

Vo-Dinh; "Biosensors, Nanosensors and Biochips: Frontiers in Environmental and Medical Diagnostics"; Oak Ridge National Laboratory; The 1st International Symposium on Micro & Nano Technology; Mar. 2004; 6 pages.

Vo-Dinh, et al.; "Surface-enhanced Raman Scattering (SERS) Method and Instrumentation for Genomics and Biomedical Analysis"; Journal of Raman Spectroscopy; 1999; 9 pages.

Vo-Dinh, et al.; "Cancer gene detection using surface-enhanced Raman scattering (SERS)"; Journal of Raman Spectroscopy; Mar. 13, 2002; 6 pages.

Yakes, et al.; "Detection of Mycobacterium avium subsp. paratuberculosis by a Sonicate Immunoassay Based on Surface-Enhanced Raman Scattering"; Clinical and Vaccine Immunology; vol. 15; Feb. 2008; 8 pages.

* cited by examiner

FIBER OPTIC SERS SENSOR SYSTEMS AND SERS PROBES

CROSS-REFERENCE TO RELATED APPLICATION

This application claims priority to co-pending U.S. provisional application entitled, "FIBER OPTIC SERS SENSOR SYSTEMS AND RAMAN PROBES," having Ser. No. 60/835,673, filed on Aug. 4, 2006, which is entirely incorporated herein by reference.

This application is a Continuation-in-part of and claims priority to co-pending U.S. patent application entitled, "SURFACE ENHANCED RAMAN SPECTROSCOPY (SERS) SYSTEMS, SUBSTRATES, FABRICATION THEREOF, AND METHODS OF USE THEREOF," having Ser. No. 11/495,980, filed Jul. 28, 2006, which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/703,110, filed Jul. 28, 2005, which is entirely incorporated herein by reference.

This application is a Continuation-in-part of and claims priority to co-pending U.S. patent application entitled, "STRUCTURES HAVING ALIGNED NANORODS AND METHODS OF MAKING," having Ser. No. 11/256,385, filed Oct. 21, 2005, which claims priority to U.S. provisional application entitled, "DIRECT DEPOSITION OF ALIGNED NANOROD ARRAY ONTO CYLINDRICAL OBJECTS," having Ser. No. 60/620,810, filed Oct. 21, 2004, both of which are entirely incorporated herein by reference.

This application is a Continuation-in-part of and claims priority to co-pending U.S. patent application entitled, "SURFACE ENHANCED RAMAN SPECTROSCOPY (SERS) SYSTEMS, SUBSTRATES, FABRICATION THEREOF, AND METHODS OF USE THEREOF" having Ser. No. 11/376,661, filed on Mar. 15, 2006, which claims priority to U.S. provisional application entitled "SURFACE ENHANCED RAMAN SPECTROSCOPY (SERS) SYSTEMS, SUBSTRATES, FABRICATION THEREOF, AND METHODS OF USE THEREOF," having Ser. No. 60/662,089, filed Mar. 15, 2005, both of which are entirely incorporated herein by reference.

STATEMENT REGARDING FEDERALLY SPONSORED RESEARCH OR DEVELOPMENT

This invention was made with Government support under contract ECS 0304340 awarded by the National Science Foundation. The Government has certain rights in this invention.

BACKGROUND

Surface-enhanced Raman spectroscopy (SERS) has been used as an analytical tool to observe trace amounts of chemical and biological molecules due to its capability of giving real-time molecular vibrational information under ambient conditions. It has the advantages of using extremely small amounts of analyte without amplification or manipulation of the samples, and the extremely short time frame for acquisition of the spectra. SERS requires minimal sample preparation and is non-destructive to the sample, which allows real time analysis and great potential for multi-component analysis. The well-known Raman enhancement effect of SERS arises from either the adsorption or close proximity of an analyte to a metal substrate. The morphology of the metallic structure plays a major role in determining the magnitude of signal enhancement and sensitivity of detection. Early SERS substrates included a random distribution of roughness features produced by oxidation reduction on a metal electrode or evaporation of thin metal film on a flat substrate. Various forms of nanostructure have been explored to enhance SERS effects, for example; rough metallic surfaces by chemical etching, silver films on $TiO_2$, colloidal silver nanoparticles, silver nanoparticle arrays fabricated by nanosphere lithography, electro-deposition of silver on silver films at high potential, aligned monolayer of silver nanowires. However, many of these methods are either expensive or time consuming, and it is not easy to make reproducible substrates of the correct surface morphology to provide maximum SERS enhancements. Without uniformity and good reproducibility of the metal substrates, the attainment of reproducible spectra remains a major challenge for SERS.

Despite its extremely high and unique sensitivity, the application of SERS has not been incorporated into the development of practical in-situ analytical tool for real-time sensing or detecting. Usually SERS measurements are carried out by conventional Raman scattering spectrometer, which is bulky, expensive, and not easily accessible. Therefore, there is a need in the art to overcome these limitations.

SUMMARY

Fiber optic surface-enhanced Raman spectroscopic (SERS) systems (also referred to as "SERS system"), portable SERS systems, SERS probes, and methods of using the SERS systems and SERS probes to detect an analyte, are disclosed.

Briefly described, a representative embodiment of a fiber optic SERS sensor system of the present disclosure, among others, includes: a Raman system and a SERS probe, wherein the Raman system includes a Raman probe interfaced with the SERS probe and an optical fiber system for transmitting a light to the Raman probe from a light source and transmitting a signal light from the Raman probe to a Raman detection system; and the SERS probe includes a SERS structure and a SERS substrate, wherein the SERS structure includes a SERS substrate opening, a sample opening, a Raman probe opening, and a window, wherein the SERS substrate is disposed within the SERS substrate opening, wherein the Raman probe is disposed in the Raman probe opening that is along the longitudinal axis of the SERS structure so that light transmitted through the Raman probe passes through the window and impacts with the SERS substrate.

Briefly described, a representative embodiment of a method of detecting a compound of the present disclosure, among others, includes: providing a fiber optic SERS sensor system, wherein the fiber optic SERS sensor system includes a Raman system and a SERS probe, wherein the Raman system includes a Raman probe interfaced with the SERS probe and an optical fiber system for transmitting a light to the Raman probe from a light source and transmitting a signal light from the Raman probe to a Raman detection system; and the SERS probe includes a SERS structure and a SERS substrate, wherein the SERS structure includes a SERS substrate opening, a sample opening, a Raman probe opening, and a window, wherein the SERS substrate is disposed within the SERS substrate opening, wherein the Raman probe is disposed in the Raman probe opening that is along the longitudinal axis of the SERS structure so that light transmitted through the Raman probe passes through the window and impacts with the SERS substrate; exposing the SERS substrate to a sample; transmitting a light to the Raman probe from the light source, wherein the light is directed at the SERS substrate; and measuring a surface enhanced Raman spectroscopy (SERS) spectrum using the fiber optic SERS system.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3(a) illustrates a photograph of a SERS probe, while

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Embodiments of the present disclosure will employ, unless otherwise indicated, techniques of analytical chemistry, nanochemistry, biochemistry, molecular biology, medicine, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

Discussion

In accordance with the purpose(s) of the present disclosure, as embodied and broadly described herein, embodiments of the present disclosure, in one aspect, relate to fiber optic surface-enhanced Raman spectroscopic (SERS) systems (also referred to as "SERS system"), portable SERS systems, SERS probes, and methods of using the SERS systems and SERS probes to detect an analyte. The present disclosure provides for portable and remote applications of portable SERS systems, where embodiments of the present disclosure are field-deployable, small and compact in size with very high sensitivity, selectivity, and multiplexing ability. In addition, the present disclosure provides for an easily fabricated SERS substrate that can be used in solution for the application of SERS in in-situ analyses.

The present disclosure provides, in general, methods and systems for the detection, analysis, and/or quantification of one or more targets. One aspect, among others, provides methods and systems for the detection of a target using SERS systems including a SERS substrate including an array of nanostructures. In particular, embodiments of the present disclosure can be used to determine the presence, qualitatively and/or quantitatively, of one or more targets that include one or more types of biomolecules, cells, toxins, drugs, viruses (e.g., different types, different strands of the same type, differences within strands of the same type, and the like), bacteria, explosives, nuclear wastes, contaminants, biohazards, and other chemical and biological compounds of interest.

In general, the SERS system includes a Raman system and a SERS probe. The Raman system includes a Raman probe interfaced with the SERS probe. The Raman probe is interfaced with a Raman system via optical fibers. The Raman system includes a light source that directs light through a source optical fiber to the Raman probe. A detection signal is channeled via a detecting optical fiber in the Raman probe to the Raman system where the signal is detected and analyzed. In this regard, the Raman system includes a Raman detection system and analysis system for qualitatively and/or quantitatively analyzing the detected signal. Embodiments of the Raman system include a light source such as, but not limited to, a diode laser, an optical fiber laser, a dye laser, a solid state laser, and a gas laser. The Raman system can include a notch filter, a spectrometer, or a monochromator, a photodetector (single detector or CCD), and corresponding computer control and analysis software.

Figure 3A:
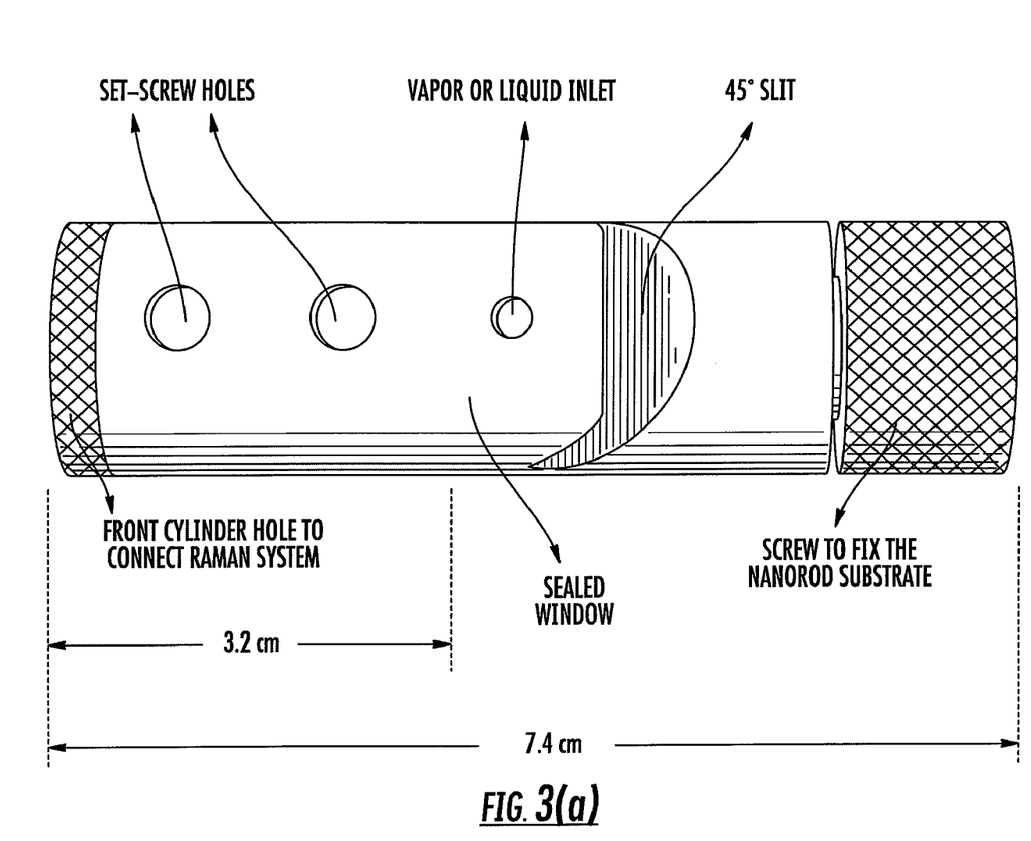

The SERS probe includes, but is not limited to, a SERS probe structure and a SERS substrate. The SERS probe structure can include a SERS substrate opening, a sample opening, and a Raman probe opening, and a window. The SERS substrate opening can receive the SERS substrate. The sample opening can receive a sample (e.g., liquid or gas). The Raman probe opening can receive the Raman probe. In addition, the SERS probe structure may include one or more openings to secure one or more of the Raman probe and the SERS substrate. The openings can be treaded for a screw or be designed for other securing mechanisms (See FIG. 3(a) in Example 1).

The SERS probe structure includes a window or transparent structure disposed between the Raman probe opening and the SERS substrate opening. The window can be made of materials such as, but not limited to, glass, quartz, and sapphire. The window is positioned substantially perpendicular to the longitudinal axis of the SERS probe structure.

In general, the SERS probe structure can be interfaced with a SERS substrate. The interface includes the SERS substrate opening (e.g., a slit) in the SERS structure, where the SERS substrate opening can receive the SERS probe. In an embodiment, the opening is in the side of the SERS probe structure and places the SERS probe at an angle relative to the longitudinal axis of the SERS probe structure (e.g., about 45° relative to the axis perpendicular the longitudinal axis).

In an embodiment, a sample can be introduced to the SERS probe through the sample opening in the SERS probe structure. The sample opening in the SERS probe structure can include a pathway into the SERS probe structure that interfaces with the SERS probe to dispose the sample onto the surface of the SERS probe, and subsequently be detected. In another embodiment, the SERS probe can be exposed to a sample prior to being disposed in the SERS probe structure. Thus, the SERS probe having the sample disposed thereon can be disposed within the opening of the SERS probe structure to detect the presence of the sample on the surface of the SERS probe.

The Raman probe can be interfaced with the SERS probe structure via the Raman probe opening. In an embodiment, the Raman probe opening is at one end of the SERS probe structure in line with the longitudinal axis of the SERS probe structure. In this regard, the Raman probe can direct a light from a light source (e.g., a laser) at the SERS substrate. As mentioned above, the SERS substrate is positioned within the SERS probe structure at an angle (e.g., about 45°) relative to the longitudinal axis of the SERS probe structure. Thus, the SERS substrate is positioned at an angle (e.g., about 45°) relative to light from the Raman probe. In this regard, the relative positions of the light and the SERS substrate can be altered to maximize the detection ability of the SERS system.

The SERS substrate includes an array of nanostructures disposed on the surface of the SERS substrate. The nanostructures can include, but are not limited to, nanorods, nanowires, nanotubes, nanospirals, combinations thereof, and the like, and uniform arrays of each. The nanostructures (e.g., nanorods) can be fabricated of one or more materials such as, but not limited to, a metal, a metal oxide, a metal nitride, a metal oxynitride, a metal carbide, a doped material, a polymer, a multicomponent compound, a compound (e.g., a compound or precursor compound (organic or inorganic compound) including a metal, a metal oxide, a metal nitride, a metal oxynitride, a metal carbide, a doped material), and combinations thereof. The metals can include, but are not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof. In particular the materials can include one or more of the following: silver, gold, nickel, silicon, germanium, silicon oxide, and titanium oxide. The composition of the nanorods is the same as that of the materials described herein or a combination of the materials described herein, or alternative layers of each.

In an embodiment of the SERS substrate of the present disclosure, the nanostructure is a nanorod. In particular embodiments, the nanorod is formed in a uniform and aligned array on the substrate. The nanorod can have the dimensions and characteristics as described below. In particular, the nanorods (e.g., silver, nickel, silicon, and titanium oxide) are disposed on a planar substrate, such a glass or silicon slide or disk, or a non-planar substrate, such as an optical fiber, or other cylindrically symmetric substrates.

In preferred embodiments, the nanostructure is a nanorod (nanocolumn). In an exemplary embodiment, the nanostructure is functionalized with one or more binding agent(s) capable of binding (e.g., ionically covalently, hydrogen binding, and the like) or otherwise associating (e.g., chemically, biologically, etc.) with one or more analytes (e.g., compound or biomolecule) of interest.

A method of making a SERS substrate of the present disclosure includes providing a substrate and depositing the nanorods on the substrate by a modified oblique angle deposition (OAD) technique/system or glancing angle deposition (GLAD). In an embodiment of a modified OAD technique, the OAD system can include a two-axis substrate motion apparatus in a physical vapor deposition (PVD) system (e.g., thermal evaporation, e-beam evaporation, sputtering growth, pulsed laser deposition, and the like) that operates at temperatures lower than the melting point of the material used to form the nanostructures. In an embodiment, the substrate motion system provides two rotation movements: one is the polar rotation, which changes angle between the substrate surface normal and the vapor source direction, and one is the azimuthal rotation, where the sample rotates about its center axis of rotation (e.g., normal principle axis). In some embodiments, the nanorods are disposed on a thin film (e.g., silver, nickel, silicon, and titanium oxide) or a multilayer thin film (e.g., layers of silver, nickel, silicon, and titanium oxide, composites thereof, and nitrides thereof) that is deposited onto those substrates prior to nanorod deposition.

At least one advantage of using the OAD system is that the nanostructures (e.g., nanorods) can be formed at temperatures compatible with substrates such as, but not limited to, optical fibers, waveguides, and the like. This is in contrast to other techniques that operate under conditions (e.g., high temperatures) that are not compatible with many substrates of interest. Another advantage of using the OAD system is that catalysts are not needed to form the nanostructures, in contrast to currently used technologies. Since a vacuum system is used, the purity of the nanorods is very high, and the vacuum system is compatible with conventional microfabrication processes.

In some embodiments the substrate is a planar (or flat) substrate, such as silicon, quartz, or glass substrate. Planar substrates may also be made of materials including, but not limited to, semiconductors (e.g., Si, GaAs, GaAsP, and Ge), oxides (e.g., $SiO_2$, $Al_2O_3$), and polymers (e.g., polystyrene, polyacetylene, polyethylene, etc.). In other embodiments the substrate is a non-planar substrate such as a cylindrical or conical substrate (e.g., an optical fiber or pipette tip). The substrates can also be microfabricated or nanofabricated substrates, such as substrates with a regular array of micropatterns, such as a dot array, line array, or well array, or similar nanopatterns.

The length is the largest dimension of the nanostructure and is the dimension extending from the substrate. The length/height of the nanorod can be from a few hundred nanometers or less to over a few thousand nanometers. In embodiments, the nanostructure can have a length of about 10 nm to 10000, about 10 nm to 5000 nm, about 10 nm to 4000 nm, about 10 nm to 3000 nm, about 10 nm to 2000 nm, about 10 nm to 1000 nm, about 10 nm to 500 nm, about 10 nm to 250 nm, about 10 nm to 100 nm, and about 10 nm to 50 nm. In particular, the nanostructures can have a length of about 100 nm to about 1500 nm. The length depends, at least in part, upon the deposition time, the deposition rate, and the total amount of evaporating materials. The substrate can have nanorods of the same height or of varying heights on one or more portions of the substrate.

The diameter is the dimension perpendicular to the length. The diameter of the nanostructure is about 10 to 30 nm, about 10 to 60 nm, about 10 to 100 nm, or about 10 to 150 nm. In particular, the nanorods can have a diameter of about 50 to 120 nm. One or more of the dimensions of the nanostructure could be controlled by the deposition conditions and the materials.

The substrate can have from tens to tens of thousands or more nanorods formed on the substrate. The array of nanostructures can be defined as having a distance of about 10 to 30 nm, about 10 to 60 nm, about 10 to 100 nm, about 10 to 150 nm, and about 10 to 200 nm, between each of the nanostructures. Alternatively, the array of nanostructures can be defined as having an average density of about 11 to $2500/\mu m^2$. The number of nanorods, height and diameter of the nanorods, and the material that the nanorods of fabricated of will depend upon the specific application of the SERS system.

In embodiments of the SERS substrates of the present disclosure, the nanorods also have a tilt angle, $\beta$, formed between the nanostructure and the substrate. The angle $\beta$ is less than 90° and can be about 50° to 85°, or about 70° to 75°.

Additional details regarding the SERS substrate are described in U.S. patent application having Ser. No. 11/495,980, filed Jul. 28, 2006; U.S. patent application having Ser. No. 11/256,385, filed Oct. 21, 2005, and U.S. patent application having Ser. No. 11/376,661, filed on Mar. 15, 2006, each of which are incorporated herein by reference.

Figure 1:
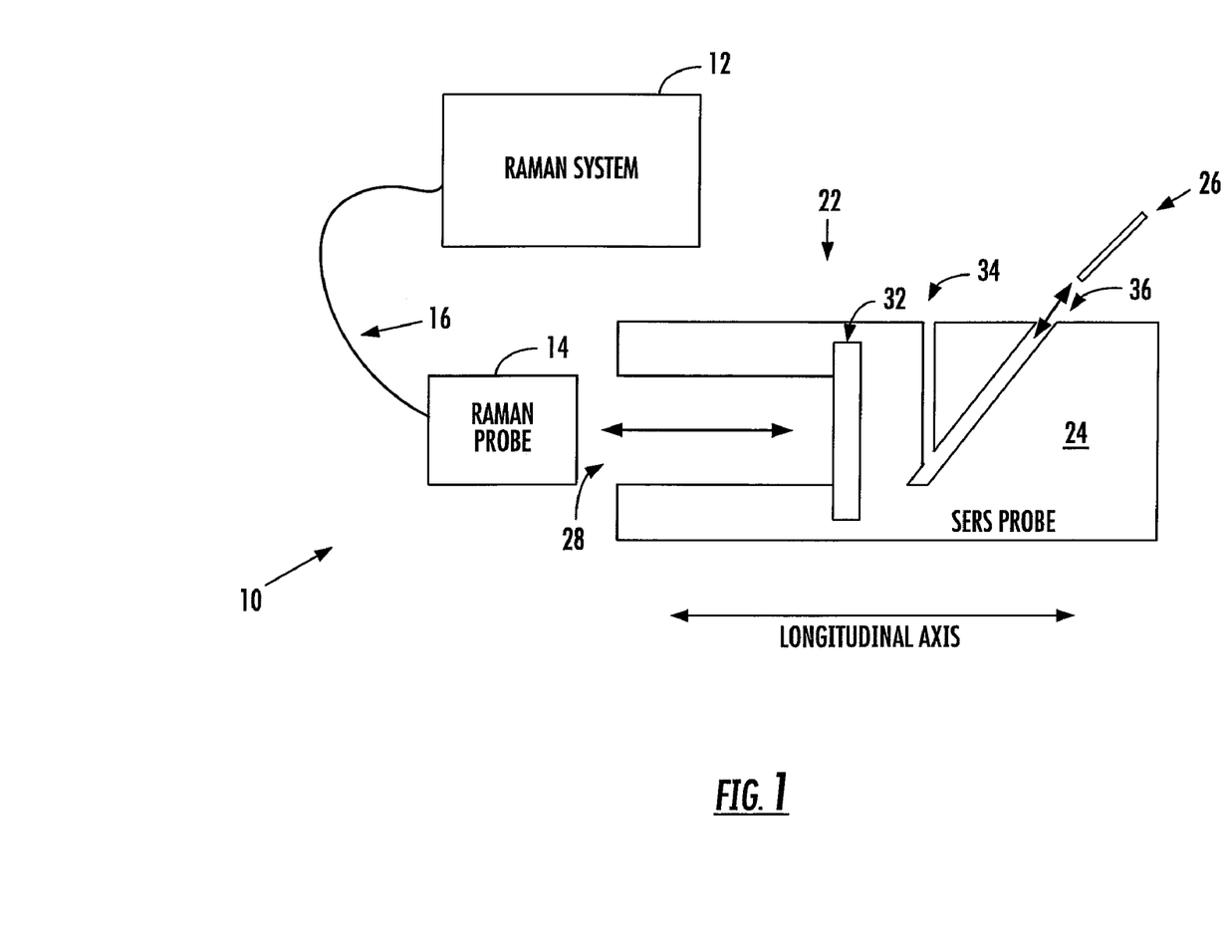
FIG. 1 illustrates an embodiment of a fiber optic SERS system.

FIG. 1 illustrates an embodiment of a SERS system 10. The SERS system 10 includes, but is not limited to, a Raman system 12 and a SERS probe 22. The Raman system 12 includes, but is not limited to a Raman probe 14, a detection system, and other components, where the Raman probe 14 is interfaced with the detection using one or more optical fibers 16. The SERS probe 22 includes, but is not limited to, SERS probe structure 24 and a SERS substrate 26. The SERS probe structure 24 includes, but is not limited to, a Raman probe opening 28, a window 32, a sample opening 34, and a SERS substrate opening 36. The SERS probe structure 24 may include one or more openings that can be used to secure the Raman probe 14 and/or the SERS substrate 26.

Embodiments of the SERS system can be portable. In this regard the Raman probe and the SERS probe structure can be designed to be of a portable size (in the range of centimeters). In particular, the length of the Raman probe and the SERS probe structure can be about 5 to 10 cm, about 10 cm, or in some embodiments more than 10 cm. The Raman probe and the SERS probe structure can each have a circular or square shape. In an embodiment, the Raman probe and the SERS probe structure are circular and have a diameter of about 10 mm and 20 mm, respectively, but could be from 5 mm to a few centimeters. The Raman probe opening should have a diameter sufficient to securely engage the Raman probe. In an embodiment, the Raman probe opening is about 10 mm. The sample opening should have a sufficient diameter (e.g., about 1 mm or so) to allow the sample (e.g., liquid or gas) to enter the SERS probe structure. The SERS substrate opening should have a sufficient diameter (e.g., about 1 mm or so) to allow the SERS substrate to enter the SERS structure. The window can have a thickness of about 0.1 mm to 2 mm. The window can have a length of about the diameter (e.g., about 10 mm) of the Raman probe opening.

The SERS system can be constructed by disposing the Raman probe into the Raman probe opening of the SERS probe. The Raman probe can be interfaced to the Raman system using one or more optical fibers. An embodiment of the SERS system can be operated by exposing the SERS substrate to a sample (e.g., liquid or gas). The SERS substrate can be exposed to a sample via the sample opening in the SERS probe structure or by exposing the SERS substrate to the sample prior to disposing the SERS substrate into the SERS substrate opening. Light can be directed from the Raman system to the Raman probe via the optical fiber. The Raman probe can direct the light through the window of the SERS probe structure onto the SERS substrate. A Raman signal from the sample can be directed to the Raman system via one or more optical fibers, where the signal is detected and analyzed.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

Example

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Experimental

Figure 2:
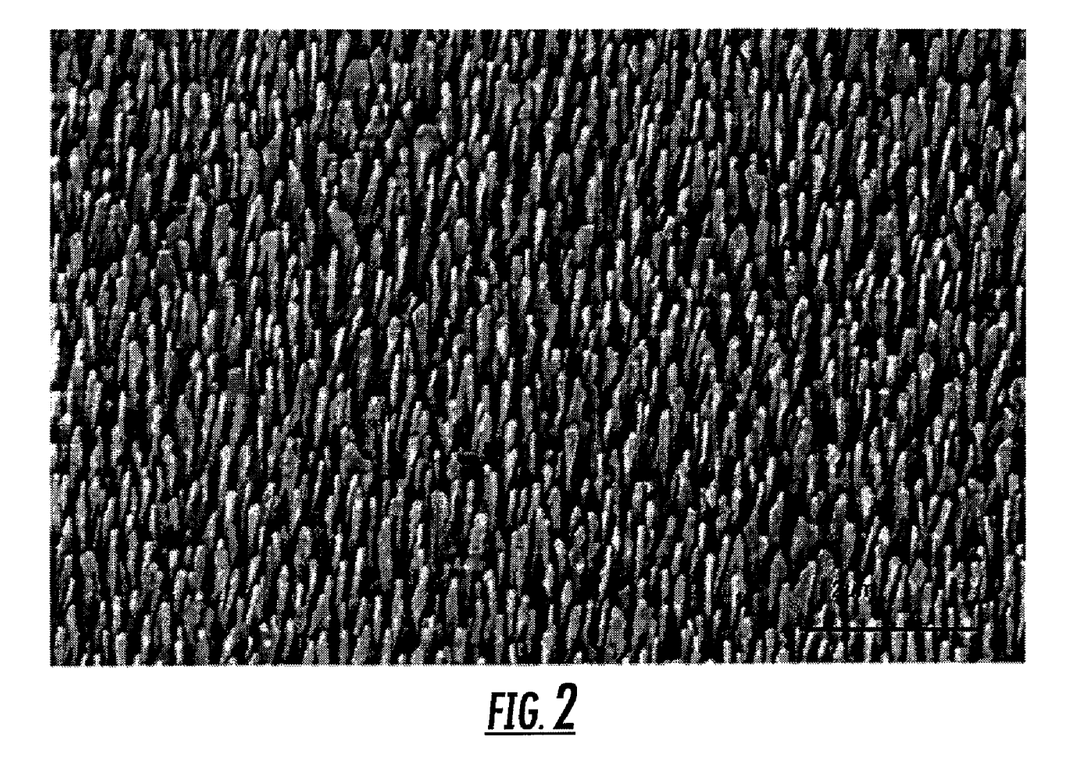
FIG. 2 illustrates a typical scanning electron microscope (SEM) image of silver nanorods array. The Ag nanorods had an average length of 868±95 nm and an average diameter of 99±29 nm. The scale bars represent 2 μm.

Silver nanorod substrates were fabricated by OAD technique using a custom-designed electron beam/sputtering evaporation (E-beam) system (Torr International, New Windsor, N.Y.) that has been described previously (Appl. Phys. Lett. 87, 031908 (2005), which is incorporated by reference). Glass microscopic slides (Gold Seal® Catalog No. 3010) were used as base platform for Ag nanorod arrays deposition. The glass slides were cleaned with Piranha solution before loading into the E-beam system. A base layer of 500 nm silver film was first deposited onto the glass slides before arrays of Ag nanorod with length of approximately 1 µm was deposited on the silver base layer by OAD at a vapor incident angle of 86°. The deposition rate was 0.3 nm/s, at a pressure of approximately $1\times10^{-6}$ Torr. The film thickness was monitor by a quartz crystal microbalance positioned at normal incidence to the vapor source direction. FIG. 2 shows a typical scanning electron microscope (SEM) image of Ag nanorod surface. The Ag nanorods had an average length of 868±95 nm and an average diameter of 99±29 nm. The average density of the nanorods was approximately 13±0.5 rods/$\mu m^2$. The average tilting angle of the nanorods was ~73°.

The fiber Raman system (also referred to as "SERS system") used in this study was the HC-10HT Raman Analyzer (Enwave Optronics Inc., Irvine, Calif.). This system is made up of a diode laser, spectrometer, an integrated Raman probe head for both excitation and collection, and separate excitation and collection fibers. The excitation source is frequency stabilized, narrow linewidth near IR diode laser with a wavelength of 785 nm. The excitation laser beam was coupled to a 100 µm fiber and is focused onto the substrate through the Raman probe head and is unpolarized at the sample. The focal length of the Raman probe is 6 mm, and the diameter of the focal spot is 1 mm. The Raman signal from the substrate is collected by the same Raman probe head and is coupled to a 200 µm collection fiber, which delivers the signal to the spectrometer equipped with a charge coupled device (CCD) detector.

Figure 3B:
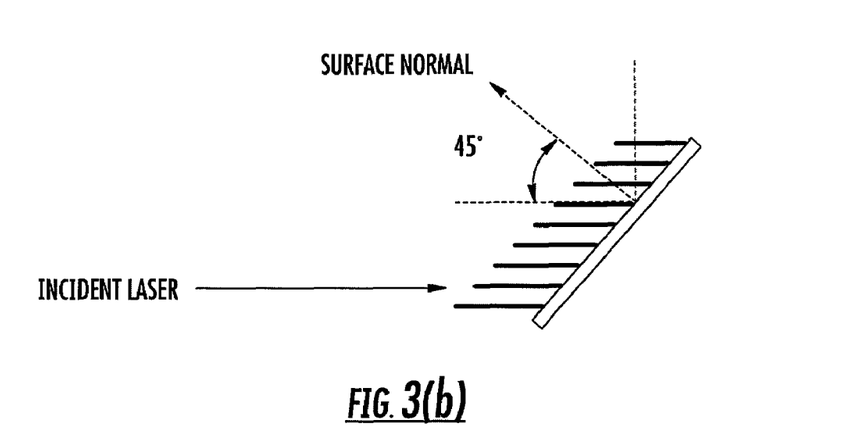
FIG. 3(b) is a schematic of the tilting Ag nanorods parallel to the incident plane at 45° incident angle relative to surface normal.
Figure 4:
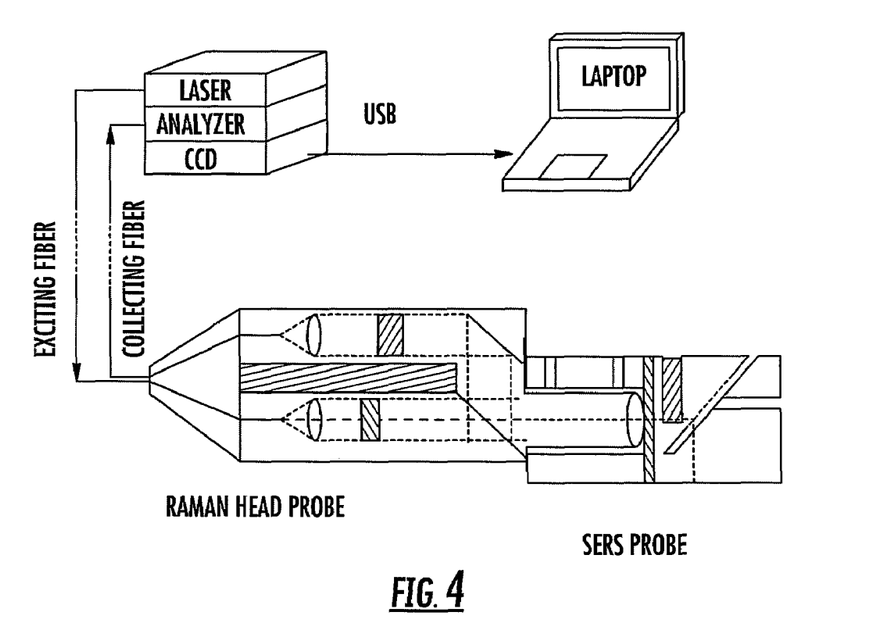
FIG. 4 illustrates schematics of the fiber Raman setup for a SERS measurement.

A portable and miniature Ag nanorod substrate based SERS probe structure with a 45° slit was designed to achieve the optimum experimental configuration and ensure maximum SERS scattering response from Ag nanorod arrays. The cylinder shape custom-designed probe measured 7.4 cm in length and 2 cm in diameter. The front of the probe opens with a cylinder hole that is 9.8 mm in diameter for connecting with the Raman Analyzer. At 3.2 cm into the SERS probe structure, there is a glass sealed window protecting the Raman head probe from the liquid or vapor. Right next to the sealed window is the liquid or vapor cell with an inlet (FIG. 3(a)). Following the liquid cell is a slit that is a substrate holder that makes the incoming laser beam focus onto the substrate at 45° incident angle to the substrate surface normal. The distance between the sealed window and the center of holder is around 5.2 mm so that the laser beam can focus on the substrate. The Ag nanorod substrates prepared by OAD technique are put into the SERS probe structure through the open slit, facing the fiber optic Raman probe head. The tilting plane of the Ag nanorods is parallel to the incident plane at 45° incident angle relative to surface normal (FIG. 3(b)). Through the SERS fiber probe, a SERS signal can be obtained by Raman Analyzer (FIG. 4).

The molecular probe used in this study was trans-1,2-bis (4-pyridyl)ethene (BPE, 99.9+%, Sigma, St. Louis, Mo.). BPE solutions were prepared by sequential dilution in HPLC grade methanol (Aldrich) or distill water. For each concentration, a 2 µL drop of BPE solution was consequently applied onto the Ag nanorod substrate and allowed it to dry before the acquisitions of data. SERS spectra were collected from multiple spots on samples.

Results and Discussion

SERS Probe Detection Limit of BPE

Figure 5:
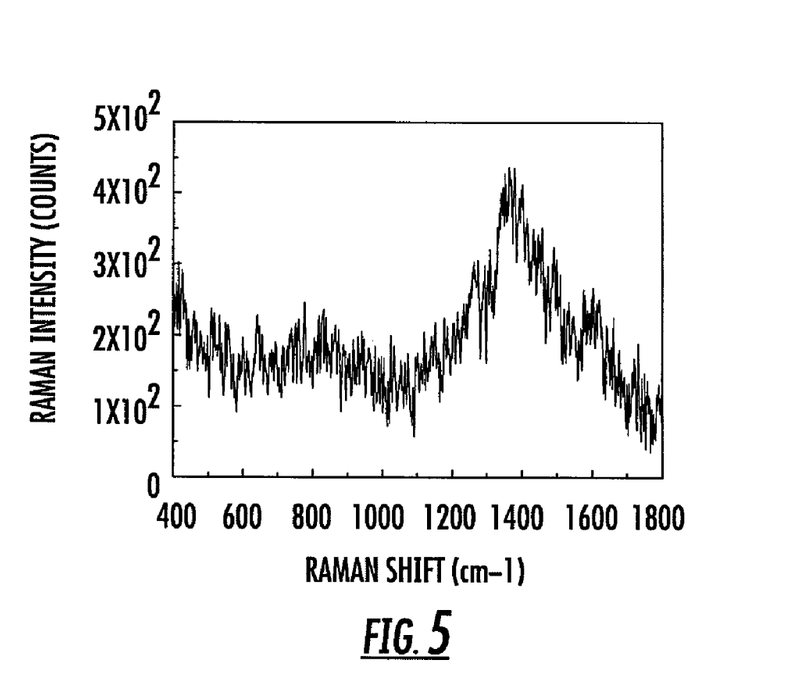
FIG. 5 illustrates a typical SERS spectrum of bare substrate. The spectrum was collected at an excitation wavelength of 785 nm, laser power of 52 mW and collection time of 10 s.

The SERS signals of BPE were acquired by a fiber Raman system at an excitation wavelength of 785 nm. FIG. 5 shows the representative SERS spectrum of a bare Ag nanorod substrate measured after the fabrication process and before BPE molecules were deposited on the substrate. A broad peak can be seen around 1360 $cm^{-1}$. Vapor deposited silver films and electrochemically reduced silver electrodes have been reported to exhibit backgrounds due to graphitic carbonaceous adsorption onto the substrate during deposition. The peak around 1360 $cm^{-1}$, ascribed to disorder in the carbon chains, is most possibly contaminant during the fabrication process and storage in ambient environment. Such background signals are commonly found in SERS. Similar spectra from multiple spots on the same Ag nanorods substrate or from different substrates showed no difference in peak position and the intensity remained unaffected under laser irradiation.

Figure 6:
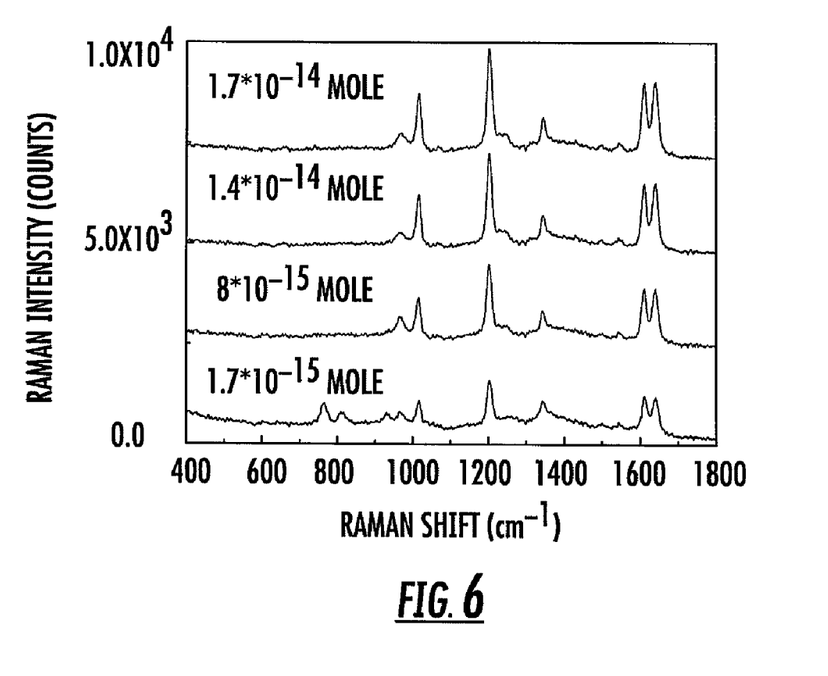
FIG. 6 illustrates a SERS spectra of BPE deposited on Ag nanorod substrate. The amount of adsorbed BPE on substrate was calculated to be from $10^{-17}$ to $10^{-16}$ moles. The spectra were collected at an excitation wavelength of 785 nm, incident laser power of 52 mW on the samples and collection time of 10 s. Spectra were offset for clarity.

BPE was chosen as the molecular probe because of its high Raman scattering cross section and its strong and irreversible ability to adsorb onto a silver substrate. Besides being centrosymmetric, BPE is not resonantly enhanced in the visible region and exhibits very intense SER spectra using relatively modest laser powers. One drop of 2 µl BPE solutions with different concentrations, $10^{-7}$ M, $10^{-6}$ M, $10^{-5}$ M, $10^{-4}$ M and $10^{-3}$ M was subsequently applied onto the silver nanorod substrate, the sample spot formed on the substrate measured with a diameter of approximately 1.2 cm. The estimated BPE molecular coverage on the surface ranged from $1.5\times10^{-4}$ (at 2 µl of $10^{-7}$ M) to 1.5 (at 2 µl of $10^{-3}$ M) monolayer, assuming $7\times10^{14}$ BPE molecules per $cm^2$ in a monolayer. The amount of BPE on the laser spot was approximately $1.4\times10^{-17}$ to $1.4\times10^{-13}$ moles. FIG. 6 shows the SERS spectra of different amount of adsorbed BPE, from $1.4\times10^{-17}$ to $1.4\times10^{-16}$ moles, on Ag nanorod substrate. All spectra show the characteristic peaks of BPE at around 1200 $cm^{-1}$, 1610 $cm^{-1}$ and 1640 $cm^{-1}$, corresponding to ethylenic C=C stretch mode, pyridine ring C=C stretch, and the whole ring C=C stretching mode respectively. The broad peak around 1360 $cm^{-1}$ from substrate background remained unchanged during the study. Thus, it does not present as a significant interference peak in the BPE spectra. These results demonstrate that integrated SERS probe could detect approximately 14 attomole of BPE on Ag nanorod arrays prepared by OAD method with very good signal-to-noise ratio spectra.

Figure 7:
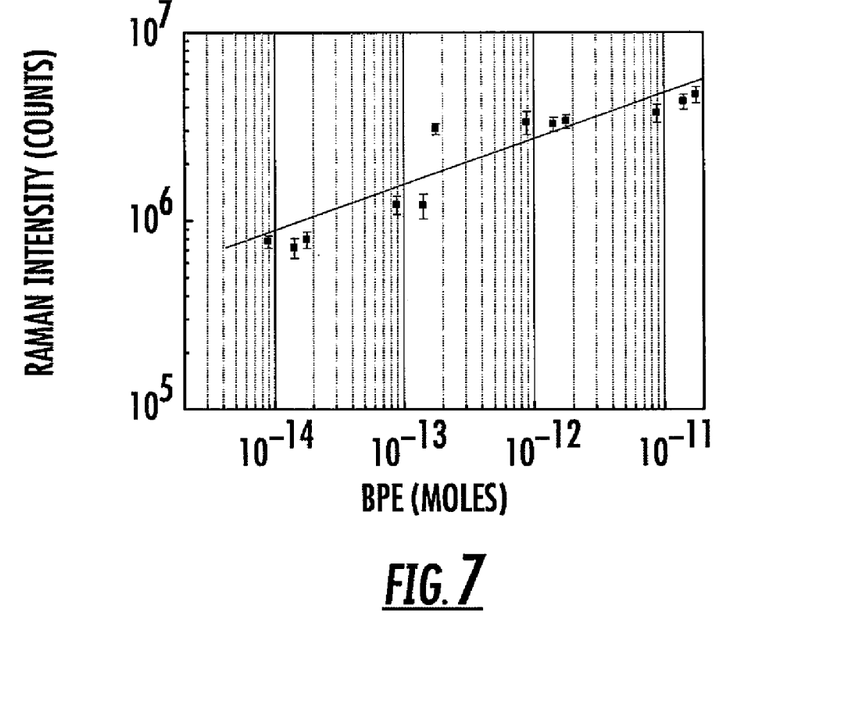
FIG. 7 illustrates a graph of the Log-log plot of the integrated band areas at 1200 $cm^{-1}$ in the SERS spectra of BPE against the number of moles of BPE deposited onto the Ag nanorod substrate surface. Spectra were collected from 5 spots for each application of BPE at an excitation wavelength of 785 mm, incident laser power of 52 mW on the samples and collection time of 10 s. The average intensities were plotted and the error bars represent the standard deviation values.

In order to study the concentration of BPE in connection with SERS intensity, the SERS response of the Ag nanorod substrates for increasing surface coverage of BPE was measured. Increasing amounts of BPE were consecutively applied onto the Ag nanorod substrate and SERS spectra were collected for each application of BPE. Collecting multiple spectra from a single spot can cause loss of SERS intensity as a result of sample degradation or the molecules bleached on the spot. To avoid such possible artifacts in the data, spectra were obtained from 5 spots on the same substrate. FIG. 7 shows the integrated band areas of the 1200 $cm^{-1}$ peak plotted against the moles of BPE put down on the Ag nanorod substrate in a log-log scale. The 1200 $cm^{-1}$ peak of BPE was chosen for the quantification due to its relative insensitivity to molecular orientation on a silver surface. As shown in FIG. 7, the Raman intensity increases as the BPE molecules adsorbed on the Ag nanorod substrate increases. The SERS signal from BPE increase over 3 orders of magnitude (14 attomoles to 14 femtomoles), after which point the further increase in Raman intensity was barely remarkable. This reflects that the saturation of the intensity occurred between the estimated surface coverage of ~0.7 and 1.5 monolayer. It has been established that, on silver surface, maximum enhancement is observed when a monolayer of the adsorbate molecule is formed on the surface. According to the fast decay of the local electromagnetic field as moving away from the metallic surface, SERS spectra are optimized when a single layer of molecules is adsorbed on the substrate. Though not the dominant role, interadsorbate interactions have been found to play some role in determining the coverage dependence. Depending on the size and shape of the particles, interadsorbate interactions can either decrease or increase the intensity. Decrement in the SERS response often occurs at high surface coverage and could be attributed to these intermolecular interactions. Though different model molecules and different substrate structures were used, the common observation in coverage dependence studies suggested the SERS intensity dependence can be established in a certain range of concentrations and surface coverage. A comparison study of sensitivity on different SERS substrates reported detection limits between 270 and 0.4 femtomole for BPE. These differences depended on the substrates with the lowest detection of 0.4 femtomole found on vapor deposited annealed silver film (~5 nm) and a reduction in the SERS response occurred at coverage greater than ~0.01 monolayer. Another study reported approximately 50-200 µM detection limits for BPE on etched silver foil and vapor deposited silver film. In this study of SERS probe detection of BPE, our results showed that the portable probe has a sensitivity of 14 attomole for BPE. We also demonstrated the concentration dependent of Raman intensities of BPE on the OAD fabricated silver nanorod array. It is difficult to make direct comparisons between various substrates based on the literature since the available data were acquired with different instruments, exposure time and environmental conditions. However, unlike most SERS measurement carried out by a bulky Raman spectrometer which is not feasible for remote function, our SERS probe provides the advantage of easy implementation, mobility and compact size for real-time, on-site field application.

SERS Signal of BPE as Function of Time

Response time and stability of the SERS signal with time are two important analytical parameters. In order to utilize our integrated SERS probe fiber Raman system for in-situ measurement, the time evolution of the SERS signal of aqueous BPE on the silver nanorod substrate was studied. Distilled water was used as a solvent instead of methanol because methanol evaporates much faster than water; therefore, it is unsuitable for long observation time. A fresh silver nanorod substrate was first secured onto the SERS probe through the 45° slit. Then 50 µl of $10^{-6}$M BPE aqueous solution was applied to the substrate through the liquid inlet, the diameter of the sample area on the substrate submerged in the liquid cell was measured to be about 7 mm. The SERS spectra were collected at a 10 min interval as BPE accumulated on the surface over a period of 80 min. BPE solution was sucked out of the liquid inlet before the next higher concentration was added.

Figure 8:
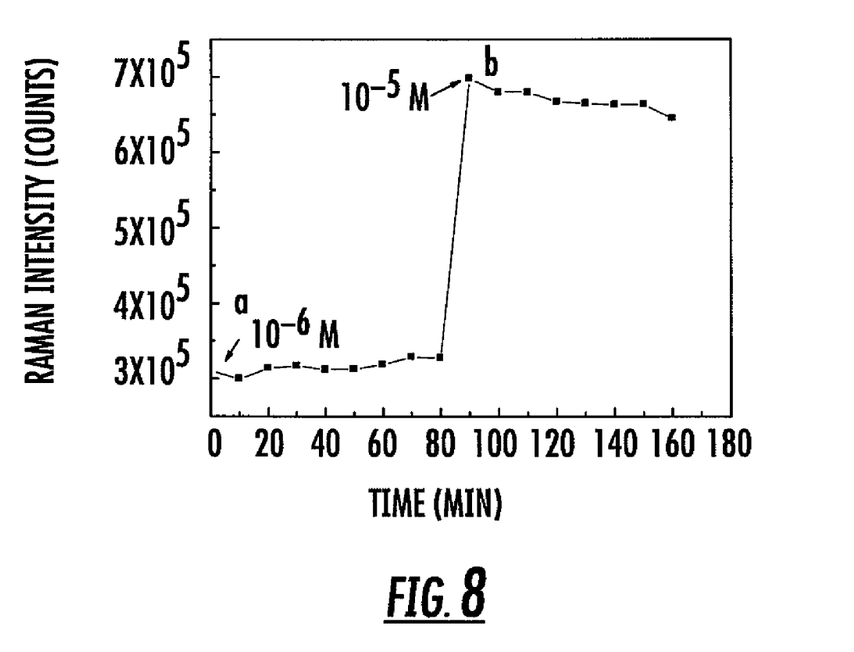
FIG. 8 illustrates a plot of the integrated band areas at 1200 $cm^{-1}$ in the SERS spectra of BPE as a function of time. The concentrations of BPE are from $10^{-6}$ to $10^{-5}$ M. DI water was used as solvent. BPE solution was drawn out of the liquid cell before the next higher concentration was added. The elapsed time for each concentration was 80 min. The spectra were collected at an excitation wavelength of 785 nm, laser power of 96 mW and collection time of 10 s.

FIG. 8 shows the plot of the integrated band areas at 1200 $cm^{-1}$ in the SERS spectra of BPE as a function of time. The graph shown in FIG. 6 indicates the equilibrium of the BPE molecules between the water and the substrate was reached in 60 min after the addition of $10^{-6}$M BPE. Though a higher laser power was used to acquire higher intensity for the in-situ measurement, the substrate was only exposed to the laser beam during the spectra acquisition to avoid photodecomposition of the analyte. Any substrate surface heating that may have been caused by the incident laser beam would have been dispersed instantly since the substrate was in contact with the liquid medium, which served as a heat sink. Furthermore, when any photodecomposition of the sample occurred at the substrate surface, the decomposed sample molecule could have diffused into the sample solution while being replaced by another BPE molecule from the solution. The increasing SERS signals over the first 80 min elapsed time indicate that BPE molecules were not thermally degraded with time. As expected, the Raman intensity increased when the higher concentration of BPE solution ($10^{-5}$M) was added on the substrate. In 10 min after adding the BPE solution ($10^{-5}$M), the SERS signal appeared to be on a slight decline. In the study of SERS effect of BPE on gold particle arrays, Félidj et al reported that by immersing the array into $10^{-5}$M BPE solution, where single layer of absorbed molecules occurred, yielded the maximum Raman intensity. Increasing or decreasing this concentration in the solution lead to a weakening of the Raman signal. Assuming over time, BPE ultimately accumulated at the geometric surface area which the applied sample spread, the estimated BPE molecular coverage on the surface could have been as high as 1.1 monolayer (50 µl of $10^{-5}$M BPE, assuming $7 \times 10^{14}$ BPE molecules per $cm^2$ in a monolayer).

In FIG. 6, the slight decline of the addition of BPE solution ($10^{-5}$M) reflects the saturation of the Raman intensity as increasing BPE adsorbed on the surface and suggests that the single layer occurred. This result coincides with the observation from Félidj et al. The high surface coverage could explain the descent in the SERS response, considering the Raman enhancement arises mainly from the electromagnetic amplification of the local field that exponentially decreases as moving away from the surface. Another possibility for the slow decline of the SERS signal is that photodegradation of BPE molecules might have occurred at this point and caused the decay of the Raman signals. Moreover, some BPE molecules could have been lost through the dynamic equilibrium with surfaces, thus producing a smaller final concentration. It is known that solvents induce morphology changes of silver island films. The change in surface tension at the silver surface, resulting from the adsorbed solvent, could greatly perturb the morphology. Roark et al. reported thin silver film morphology changes by dip coating solvent on the surface and found the intensity of the SERS of BPE adsorbed to the silver films increased. The mechanism by which solvent induced morphology changes appears to be associated with the mechanical aspect of dip-coating, as well as changes in the surface tension, but is not due to significant loss of metal from the substrate. Li et al found the formation of infinite regular silver rings on a thin silver island film after immersing in water for 30 min and then blow dried with nitrogen gas. As the water evaporated, capillary forces drew the nanorods together and contributed to the morphology changes on the substrate. In our study, nanorod array was immersed in the aqueous BPE solution throughout the measurement period. Sealing the liquid cell with plastic Parafilm wrap delayed the evaporation of water, therefore preventing the capillary force changing the morphology of silver nanorod substrate. We focus our attention on the in-situ measurement of the SERS response of aqueous BPE on the silver nanorod substrate. Over all, our data shows the concentration dependent SERS signal of BPE on the silver nanorod substrate in an aqueous environment. Our special design of the SERS probe is an adequate sample holder for performing in-situ analyses.

CONCLUSIONS

We have created a portable SERS probe that can be easily incorporated with a fiber Raman system. We demonstrated the concentration dependent of Raman intensities on the OAD fabricated silver nanorod array using BPE as molecular probe and observed a sensitivity of 14 attomole for BPE. Furthermore, we tested the response time and stability of the in situ SERS signal of BPE in a water solution on the silver nanorod substrate. Our present experiment indicates that SERS probe can be integrated into a fiber Raman system for in-situ measurements and can act as a portable and remote sensor for accurate and rapid real-time SERS measurements. It has great potential as a multiplexing system for chemical and biological sensing, such as environmental pollution, chemical and biological warfare agent detection, virus or bacteria detection, etc. This is an important development for practical SERS applications because of the possibility of using low-power laser, inexpensive substrate and compact size sensor for field applications.

Therefore, at least the following is claimed:

1. A fiber optic SERS sensor system, comprising:
a Raman system and a SERS probe, wherein the Raman system includes a Raman probe interfaced with the SERS probe and an optical fiber system for transmitting a light to the Raman probe from a light source and transmitting a signal light from the Raman probe to a Raman detection system; and
the SERS probe includes a SERS probe structure and a SERS substrate, wherein the SERS probe structure includes a SERS substrate opening, a sample opening, a Raman probe opening, and a window, wherein the SERS substrate is disposed within the SERS substrate opening, wherein the Raman probe is disposed in the Raman probe opening that is along the longitudinal axis of the SERS probe structure so that light transmitted through the Raman probe passes through the window and impacts with the SERS substrate.

2. The fiber optic SERS sensor system of claim 1, wherein the SERS substrate opening is positioned at about a 45° angle relative to the longitudinal axis of the SERS probe structure so that the SERS substrate is positioned at about a 45° angle relative to the Raman probe.

3. The fiber optic SERS sensor system of claim 2, wherein the SERS substrate has an array of nanorods on the substrate, wherein the nanorods have a length of about 10 nanometers (nm) to 1500 nm, wherein the nanorods have a width of about 50 nm to 150 nm, wherein the nanorods are at a tilting angle of about 65 to 80 degrees, and wherein a laser has an incident angle of about −10 to +60 degrees.

4. The fiber optic SERS sensor system of claim 3, wherein the nanorods are selected from one of the following materials: a metal, a metal oxide, a metal nitride, a metal oxynitride, a polymer, a multicomponent material, and combinations thereof.

5. The fiber optic SERS sensor system of claim 3, wherein the nanorods are selected from one of the following: silver, nickel, aluminum, silicon, gold, platinum, palladium, titanium, cobalt, copper, zinc, oxides of each, nitrides of each, oxynitrides of each, and combinations thereof.

6. A method of detecting a compound, comprising:
providing a fiber optic SERS sensor system, wherein the fiber optic SERS sensor system includes a Raman system and a SERS probe,
wherein the Raman system includes a Raman probe interfaced with the SERS probe and an optical fiber system for transmitting a light to the Raman probe from a light source and transmitting a signal light from the Raman probe to a Raman detection system; and
the SERS probe includes a SERS structure and a SERS substrate, wherein the SERS structure includes a SERS substrate opening, a sample opening, a Raman probe opening, and a window, wherein the SERS substrate is disposed within the SERS substrate opening, wherein the Raman probe is disposed in the Raman probe opening that is along the longitudinal axis of the SERS structure so that light transmitted through the Raman probe passes through the window and impacts with the SERS substrate;
exposing the SERS substrate to a sample;
transmitting a light to the Raman probe from the light source, wherein the light is directed at the SERS substrate; and
measuring a surface enhanced Raman spectroscopy (SERS) spectrum using the fiber optic SERS system.

7. The method of claim 6, wherein exposing includes disposing a drop of the sample into the sample opening, wherein the drop contacts the SERS substrate.

8. The method of claim 6, wherein the SERS substrate opening is positioned at about a 45° angle relative to the longitudinal axis of the SERS structure so that the SERS substrate is positioned at about a 45° angle relative to the Raman probe.

9. The method of claim 6, wherein the SERS substrate has an array of nanorods on the substrate, wherein the nanorods have a length of about 10 nanometers (nm) to 1500 nm, wherein the nanorods have a width of about 50 nm to 150 nm, wherein the nanorods are at a tilting angle of about 65 to 80 degrees, and wherein a laser has an incident angle of about −10 to +60 degrees.

10. The method of claim 6, wherein the nanorods are selected from one of the following materials: a metal, a metal oxide, a metal nitride, a metal oxynitride, a polymer, a multicomponent material, and combinations thereof.

11. The method of claim 6, wherein the nanorods are selected from one of the following: silver, nickel, aluminum, silicon, gold, platinum, palladium, titanium, cobalt, copper, zinc, oxides of each, nitrides of each, oxynitrides of each, and combinations thereof.

* * * * *

UNITED STATES PATENT AND TRADEMARK OFFICE
CERTIFICATE OF CORRECTION

| | | |
|---|---|---|
| PATENT NO. | : 7,656,525 B2 | Page 1 of 1 |
| APPLICATION NO. | : 11/834233 | |
| DATED | : February 2, 2010 | |
| INVENTOR(S) | : Zhao et al. | |

It is certified that error appears in the above-identified patent and that said Letters Patent is hereby corrected as shown below:

Title page, item (63) should read as follows.

Continuation-in-part of application No. 11/495,980, filed on July 28, 2006, now Patent No. 7,583,379, application No. 11/834,233, which is a continuation-in-part of application No. 11/376,661, filed on March 15, 2006, application No. 11/834,233, which is a continuation-in-part of application No. 11/256,395, filed on Oct. 21, 2005.

Signed and Sealed this

Twenty-seventh Day of April, 2010

David J. Kappos
*Director of the United States Patent and Trademark Office*